United States Patent [19] [11] Patent Number: 5,487,818
Cavallotti et al. [45] Date of Patent: Jan. 30, 1996

[54] PROCESS FOR SEPARATING PHTHALIMIDO-PEROXYCAPROIC ACID FROM SOLUTIONS IN ORGANIC SOLVENTS

[75] Inventors: Claudio Cavallotti; Claudio Troglia, both of Milan; Roberto Garaffa, Naples, all of Italy

[73] Assignee: Ausimont S.p.A., Italy

[21] Appl. No.: 285,927

[22] Filed: Aug. 4, 1994

Related U.S. Application Data

[63] Continuation-in-part of Ser. No. 97,839, Jul. 28, 1993, abandoned, which is a continuation-in-part of Ser. No. 28,661, Mar. 9, 1993, abandoned.

[30] Foreign Application Priority Data

Mar. 10, 1992 [IT] Italy ................... MI92A0539

[51] Int. Cl.$^6$ .......................... B01D 1/14; C07D 209/48
[52] U.S. Cl. .................. 203/41; 203/47; 203/49; 203/91; 548/473; 548/479; 8/111; 568/558; 568/561
[58] Field of Search ................... 203/49, 41, 47, 203/91; 548/473, 479; 8/111; 568/558, 561

[56] References Cited

U.S. PATENT DOCUMENTS

| 4,172,086 | 10/1979 | Berkowitz | 260/406 |
| 5,061,807 | 10/1991 | Gethofer et al. | 548/473 |
| 5,132,431 | 7/1992 | Fuchs | 548/473 |

FOREIGN PATENT DOCUMENTS

| 0325288 | 7/1989 | European Pat. Off. . |
| 0490409 | 6/1992 | European Pat. Off. . |

*Primary Examiner*—Wilbur Bascomb, Jr.
*Attorney, Agent, or Firm*—Bryan Cave

[57] ABSTRACT

A process for separating phthalimido-peroxycaproic acid (PAP) from solutions in organic solvents, wherein the organic solvents have a solubility in water equal to or lower to 10% by weight, is provided. The process employs the following steps:

(a) dispersing the solution in an aqueous medium to form a suspension;

(b) bubbling an inert gas into the resulting suspension; and (c) recovering PAP from the suspension.

13 Claims, 1 Drawing Sheet

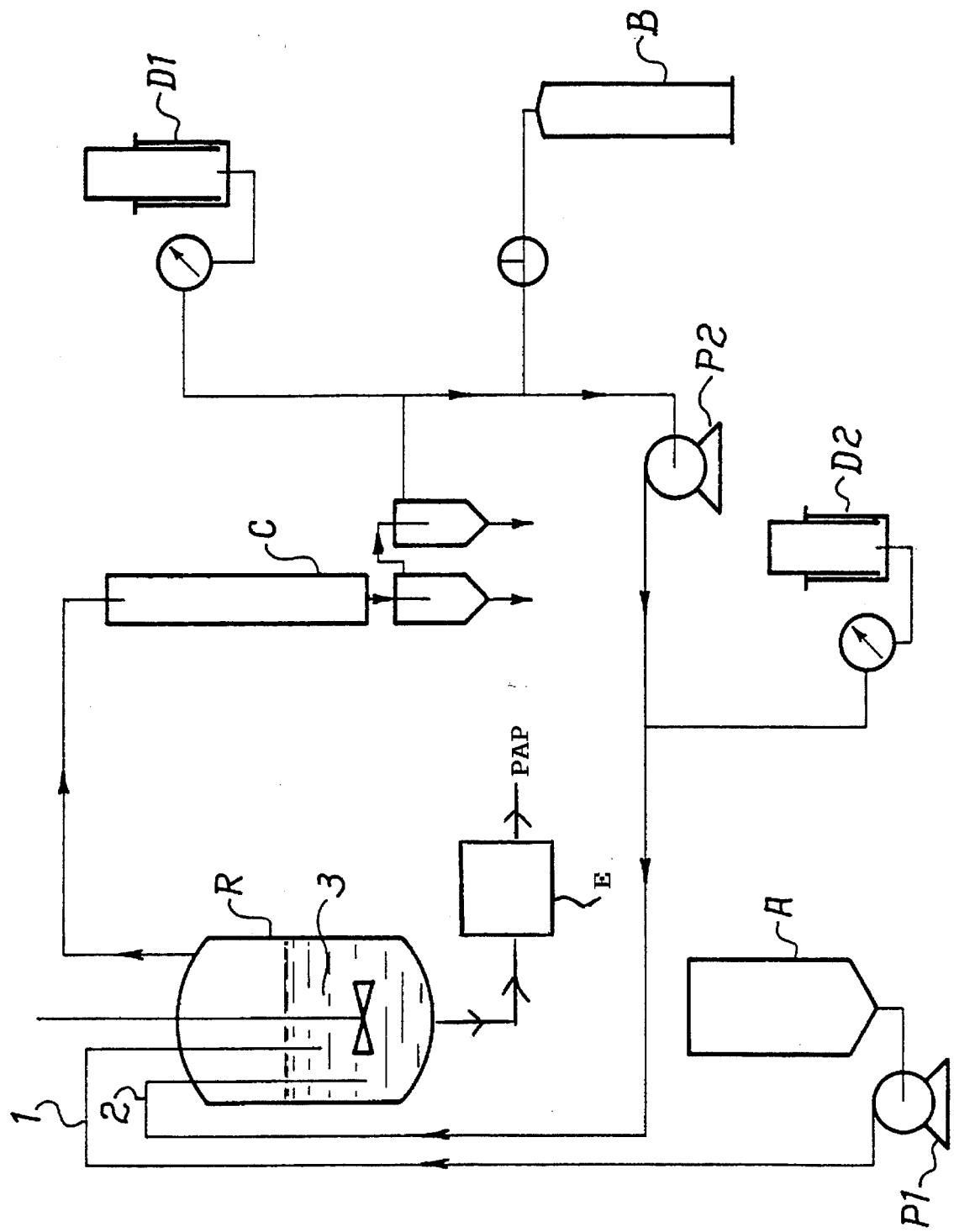

I

PROCESS FOR SEPARATING PHTHALIMIDO-PEROXYCAPROIC ACID FROM SOLUTIONS IN ORGANIC SOLVENTS

This application is a continuation-in-part application of Ser. No. 08/097,839, filed Jul. 28, 1993, now abandoned which is a continuation-in-part application of Ser. No. 08/028,661, now abandoned.

BACKGROUND OF THE INVENTION

1. Field of the Invention

The present invention relates to a process for separating phthalimido-peroxycaproic acid (PAP) from solutions in organic solvents in which it is dissolved.

In particular the present invention relates to a process for separating phthalimido-peroxycaproic acid (PAP) from its solutions in chlorohydrocarbons used in order to prepare it, and from the solutions in the other organic solvents used for its subsequent purification.

2. Description of the Prior Art

The process for preparing PAP is known from European Patent Application No. 490,409.

According to this process, phthalimido-caproic acid (PAC) is converted into the peroxyacid, by $H_2O_2$, in the presence of a strong acid, in a double-phase system, in the presence of an organic solvent constituted by a halogenated aliphatic chlorohydrocarbon selected from dichloromethane and trichloromethane. The resulting PAP is recovered from the organic phase by low-temperature crystallization, or solvent removal under vacuum.

PAP recovered in that way can be purified by recrystallization or stripping, using organic solvents as disclosed in Italian Patent Application No. HI92-A-000 381 (filed on Feb. 21st, 1992).

The processes which apply the usual separation methods display some disadvantages; for example, the organic solvent used are not completely recyclable, owing to the accumulation of impurities, or unavoidable losses the case of vacuum evaporation.

SUMMARY OF THE INVENTION

The present Applicant found now that the organic solvents can be re-used by means of a novel process used as an alternative to the usual separation methods, such as low-temperature crystallization or vacuum evaporation. This novel process makes it possible the process to be carried out under maximum safety conditions.

Therefore, the subject-matter of the present invention is a process for separating phthalimido-peroxycaproic acid (PAP) from solutions in organic solvents, characterized in that said process comprises the following steps:

- the solution of PAP in an organic solvent having a solubility in water which is equal to, or lower than, 10% by weight (1), is fed to a reactor (R) containing an aqueous medium (3), through which a stream of air or inert gas (2) is bubbled;

- the organic solvent is removed from the resulting suspension;

- the evaporated solvent is recovered in a condenser system (C); and

- PAP is recovered from the suspension.

DESCRIPTION OF THE PREFERRED EMBODIMENTS

More particularly, the subject-matter of the present invention is a process for separating phthalimido-peroxycaproic acid (PAP) from solutions in organic solvents, characterized in that said process comprises the following steps:

- the solution of PAP in an organic solvent having a solubility in water which is equal to, or lower than, by weight (1), is fed to a reactor (R) equipped with a stirring system and containing an aqueous medium (3), through which a stream of air or inert gas (2) is bubbled, at a temperature comprised within the range of from +20° C. to 40° C., and under a gauge pressure comprised within the range of from 0 to 0.266 bars (from 0 to 200 mmHg);

- the organic solvent is evaporated off from the resulting suspension, kept with stirring;

- the evaporated solvent is recovered in a condenser system (C); and

- PAP is recovered from the suspension.

Following the feeding of organic PAP solution to the aqueous medium, a suspension is obtained which derives from the precipitation of PAP in the aqueous phase.

The ratio of the aqueous medium to suspended PAP is comprised within the range of from 6 to 15 by weight, preferably of from 8 to 12 by weight,.

The temperature of the aqueous medium to which the PAP solution is fed is preferably comprised within the range of from +30° C. to 35° C.

The gauge pressure inside the reactor (R) is preferably comprised within the range of from 0.133 to 0.2 bars (from 100 to 150 mmHg).

Exemplary organic solvents for PAP, having a solubility in water equal to, or lower than, 10% by weight, and from which the separation of PAP is carried out, are chlorohydrocarbons, such as, e.g., dichloromethane and trichloromethane, aliphatic esters, such as, e.g., methyl acetate and ethyl acetate.

The aqueous medium can be constituted by demineralized water, or aqueous solutions of inorganic salts, such as, e.g., $Na_2SO_4$, $MgSO_4$, $(NH_4)_2SO_4$. If an aqueous solution of inorganic salts is used, the solution can have a concentration comprised within a wide range, preferably of from 10 to 40%. The aqueous medium can contain small amounts (0.1–3%) of substances acting as acidity neutralizers, or metal ion sequestering agents, such as, e.g., sodium or potassium salts of citric, tartaric, phosphoric, phthalic acids, or NaOH, $Na_2CO_3$, and so forth.

The inert gas used in the process can be, e.g., $CO_2$, and their mixtures.

The solvents of PAP solutions are recovered according to the process of the present invention, in a system of condensers (C) kept at a temperature not lower than 0° C., in order to prevent water entrained by the organic solvents, from solidifying. The system of condensers (C) continuously subtracts a portion of the organic solvents from the recycled gas, in such a way as to allow them to be completely recovered at the end of the operation.

According to the process of the invention, PAP is recovered from the aqueous medium by conventional recovery means, e.g., by filtration from an aqueous medium, as a crystalline powder, or granular solid, and is subsequently washed with demineralized water and dried in a desiccator ($CaCl_2$).

BRIEF DESCRIPTION OF THE DRAWING

A preferred form of practical embodiment of the process of the invention is illustrated in the flow scheme shown in

DETAILED DESCRIPTION OF THE DRAWING

According to the drawing, an organic solution of phthalimido-peroxycaproic acid (PAP) (1), coming from the feed tank (A), is fed continuously, by means of a metering pump ($P_1$), to the aqueous medium (3) which is stirred inside the reactor (R). A gas stream (2) is bubbled into the aqueous medium (3). The gas is partially constituted by inert gas drawn at the beginning of the test, from the tank (B), and partially by non-condensed vapours, continuously recycled by the pump (P2). The solvent is recovered by means of a system of condensers (C) kept at a temperature higher than 0° C. (about 5° C.). The hydraulic valves equipped with pressure gauges ($D_1$, $D_2$) are used in order to keep the pressure constant inside the equipment, preventing vapour leakages to the surrounding atmosphere. The PAP is recovered from the aqueous medium (3) through conventional recovery means (E). Preferably the PAP is recovered from the aqueous medium by filtration.

The process according to the present invention can also be performed continuously. The stirred PAP suspension can be drawn continuously, and the aqueous medium and PAP can be refilled.

The PAP separated by means of this process is of good purity. Its purity is within the range of from 96 to 99% by weight.

The process makes it possible to recover the organic solvents at a rate as high as 98% and at such a purity level that they can be used again in subsequent processes for PAP separation or purification. In such a way, the process according to the present invention is a novel separation method and can be adopted jointly with the process for PAP preparation as disclosed in European Patent Application No. 490,409.

Furthermore, the process of the present invention makes it possible to carry out the separation of PAP under maximal safety conditions, avoiding environmental pollution problems and avoiding the risk of fires or explosions due to the flammability of the used organic solvents.

In order to better understand the present invention and to practice it, some illustrative, non-limiting examples thereof are reported below.

Examples 1–3

400 g of a solution containing 18.8% by weight of PAP, 0.2% by weight of $H_2SO_4$ and 80.5% by weight of dichloromethane (deriving from the peroxidation process), was added to an aqueous medium, inside the reactor (R). The chlorinated solvent was removed through an air stream with vapours being recycled, and solvent vapours were condensed inside the system of condensers (C).

The operating conditions and the results obtained are reported in Table 1.

Example 4

400 g of a solution containing 12.31% by weight of PAP and 87.5% by weight of ethyl acetate, was added to an aqueous medium, inside the reactor (R). The organic solvent (i.e., the ester) was removed by stirring the obtained suspension, causing an $N_2$ stream to bubble through the suspension, and by recycling the non-condensed solvent vapours.

The operating conditions and the results obtained are reported in Table 1.

Examples 5 and 6 (Comparative Examples)

For comparison purposes, two tests were carried out in order to compare the separation methodology according to the present invention to the usual methodologies, such as, e.g., crystallization and vacuum evaporation.

400 g of a solution containing 18.8% by weight of PAP, and 80.5% by weight of dichloromethane was submitted to crystallization at a temperature of −5° C. in Example 5. The solution (296 g), obtained after filtration, contained 94.1% of dichloromethane and 5.9% of impurities due to the presence of phthalimido-peroxycaproic (PAP) and phthalimido-caproic acid (PAC).

According to Example 6, the solvent present in 400 g of a solution containing 14.98% by weight of PAP and 84.8% by weight of ethyl acetate was evaporated under vacuum in a rotational evaporator at a temperature of 37° C., under a residual pressure of 0.027 bars (20 mmHg).

The operating conditions and the results obtained are reported in Table 2.

The data reported in Tables 1 and 2 demonstrate that the conventional methods (Examples 5 and 6) result in a considerably lower recovery of organic solvents than the recovery obtainable by the process of the present invention. Furthermore, the data demonstrates that the solvents recovered according to the conventional methods contain significant amounts of impurities. In contrast, the solvents recovered in Examples 1–4 do not have significant amounts of impurities.

TABLE 1

| | | OPERATING CONDITIONS | | | | AQUEOUS MEDIUM | | RECOVERED SOLVENT | | OBTAINED PAP (AS DRY MATTER) | | |
|---|---|---|---|---|---|---|---|---|---|---|---|---|
| EX. | SOLVENT | SOLUTION FEED (l/h) | GAS FEED (l/h) | TEMP. (°C.) | PRESS (mmHg) | COMPOSITION | (g) | AMOUNT (g) | YIELD (%) | AMOUNT (g) | PURITY (%) | YIELD (%) |
| 1 | DI-CHLORO-METHANE | 120 | 360 | 32 | 860 | $H_2O$<br>Na-citrate | 990<br>10 | 315 | 97.8 | 74 | 98.3 | 96.7 |
| 2 | DI-CHLORO-METHANE | 120 | 360 | 32 | 860 | $H_2O$<br>$MgSO_4$<br>Na-citrate | 888<br>300<br>12 | 317 | 98.4 | 75 | 98.3 | 98.0 |
| 3 | DI-CHLORO- | 100 | 360 | 32 | 860 | $H_2O$<br>$Na_2HPO_4$ | 995<br>5 | 315 | 97.8 | 74 | 98.4 | 96.8 |

TABLE 1-continued

| EX. | SOLVENT | OPERATING CONDITIONS | | | | AQUEOUS MEDIUM | | RECOVERED SOLVENT | | OBTAINED PAP (AS DRY MATTER) | | |
| --- | --- | --- | --- | --- | --- | --- | --- | --- | --- | --- | --- | --- |
| | | SOLUTION FEED (l/h) | GAS FEED (l/h) | TEMP. (°C.) | PRESS (mmHg) | COMPOSITION | (g) | AMOUNT (g) | YIELD (%) | AMOUNT (g) | PURITY (%) | YIELD (%) |
| 4 | METHANE ETHYL-ACETATE | 90 | 300 | 37 | 860 | H₂O MgSO₄ | 450 150 | 345 | 98.6 | 49 | 98.6 | 98.1 |

TABLE 2

| COMP. EX. | SOLVENT | OPERATING CONDITIONS | | RECOVERED SOLVENT | | OBTAINED PAP (AS DRY MATTER) | | |
| --- | --- | --- | --- | --- | --- | --- | --- | --- |
| | | TEMP. (°C.) | PRESS. (mmHg) | AMOUNT (g) | YIELD (%) | AMOUNT (g) | PURITY (%) | YIELD (%) |
| 5 | DICHLOROMETHANE | −5 | — | 296 | 86.5 | 58.7 | 99.8 | 77.9 |
| 6 | ETHYLACETATE | 37 | 20 | 193 | 56.9 | 59.4 | 98.9 | 98.0 |

We claim:

1. A process for separating phthalimido-peroxycaproic acid (PAP) from a solution of PAP in an organic solvent, said organic solvent having a solubility in water equal to or lower than 10% by weight, and being selected from the group consisting of chlorohydrocarbons and aliphatic esters, said process comprising:

(a) dispersing the solution in an aqueous medium to form a suspension;

(b) evaporating the organic solvent by bubbling an inert gas into the resulting suspension; and (c) recovering PAP from the suspension.

2. The process according to claim 1, wherein the organic solvent is selected from the group consisting of dichloromethane, trichloromethane, methyl acetate, and ethyl acetate.

3. The process according to claim 1, wherein the inert gas is selected from the group consisting of air, $N_2$, $CO_2$, and mixtures thereof.

4. The process according to claim 1, wherein during step (b), the suspension is stirred.

5. The process according to claim 1, wherein in step (c), PAP is recovered by filtering the suspension.

6. The process according to claim 1, wherein the organic solvent is recovered in a condenser system.

7. The process according to claim 1, wherein step (b) is carried out at a temperature of from 20° to 40° C.

8. The process according to claim 1, wherein step (b) is carried out at a pressure of from 0 to 200 mmHg.

9. The process according to claim 8, wherein step (b) is carried out at a pressure of from 100 to 150 mmHg.

10. The process according to claim 1, wherein the ratio of the aqueous medium to the suspended PAP is from 6 to 15 percent by weight.

11. The process according to claim 1, wherein step (a) is carried out at a temperature of from 30° to 35° C.

12. The process according to claim 1, wherein the aqueous medium is an aqueous solution of inorganic salts.

13. The process according to claim 12, wherein the inorganic salts are selected from the group consisting of $Na_2SO_4$, $MgSO_4$, $(NH_4)_2SO_4$, and mixtures thereof.

* * * * *